United States Patent [19]
Mandel et al.

[11] 4,120,395
[45] Oct. 17, 1978

[54] PACKAGE FOR DOUBLE-ARMED SUTURES

[75] Inventors: Harvey B. Mandel, North Brunswick; Eberhard H. Thyen, Middlesex, both of N.J.

[73] Assignee: Ethicon, Inc., Somerville, N.J.

[21] Appl. No.: 830,372

[22] Filed: Sep. 2, 1977

[51] Int. Cl.² .................................. A61L 17/02
[52] U.S. Cl. ............................ 206/63.3; 206/227; 206/382; 206/523
[58] Field of Search ............... 206/63.3, 227, 574, 206/382, 383, 523, 472; 128/335.5, 339

[56] References Cited
U.S. PATENT DOCUMENTS

| | | | |
|---|---|---|---|
| 3,357,550 | 12/1967 | Holmes et al. | 206/63.3 |
| 3,819,039 | 6/1974 | Erickson | 206/438 |
| 3,857,484 | 12/1974 | Thyen | 206/227 |
| 3,876,068 | 4/1975 | Sonnino | 206/227 |
| 3,951,261 | 4/1976 | Mandel et al. | 206/227 |
| 3,985,227 | 10/1976 | Thyen et al. | 206/227 |
| 4,008,802 | 2/1977 | Freitag | 206/63.3 |
| 4,034,850 | 7/1977 | Mandel et al. | 206/382 |

Primary Examiner—William Price
Assistant Examiner—Bruce H. Bernstein
Attorney, Agent, or Firm—Wayne R. Eberhardt

[57] ABSTRACT

A package for double-armed sutures, particularly ophthalmic sutures, comprising a one-piece folded packet having needle mounting means and suture loop retaining means which are readily accessible when the package is opened. The needle mounting means is preferably removable to allow the suture to be withdrawn from the package with the needles secured therein. The suture loop retaining means is optionally incorporated with the needle mounting means and removable therewith. The package contains a single, double-armed suture with both needles secured in the needle mounting means and with a loop substantially equidistant from each needle retained in the suture loop retaining means so that the suture may be cut at the loop to obtain two single-armed sutures of substantially equal length.

21 Claims, 14 Drawing Figures

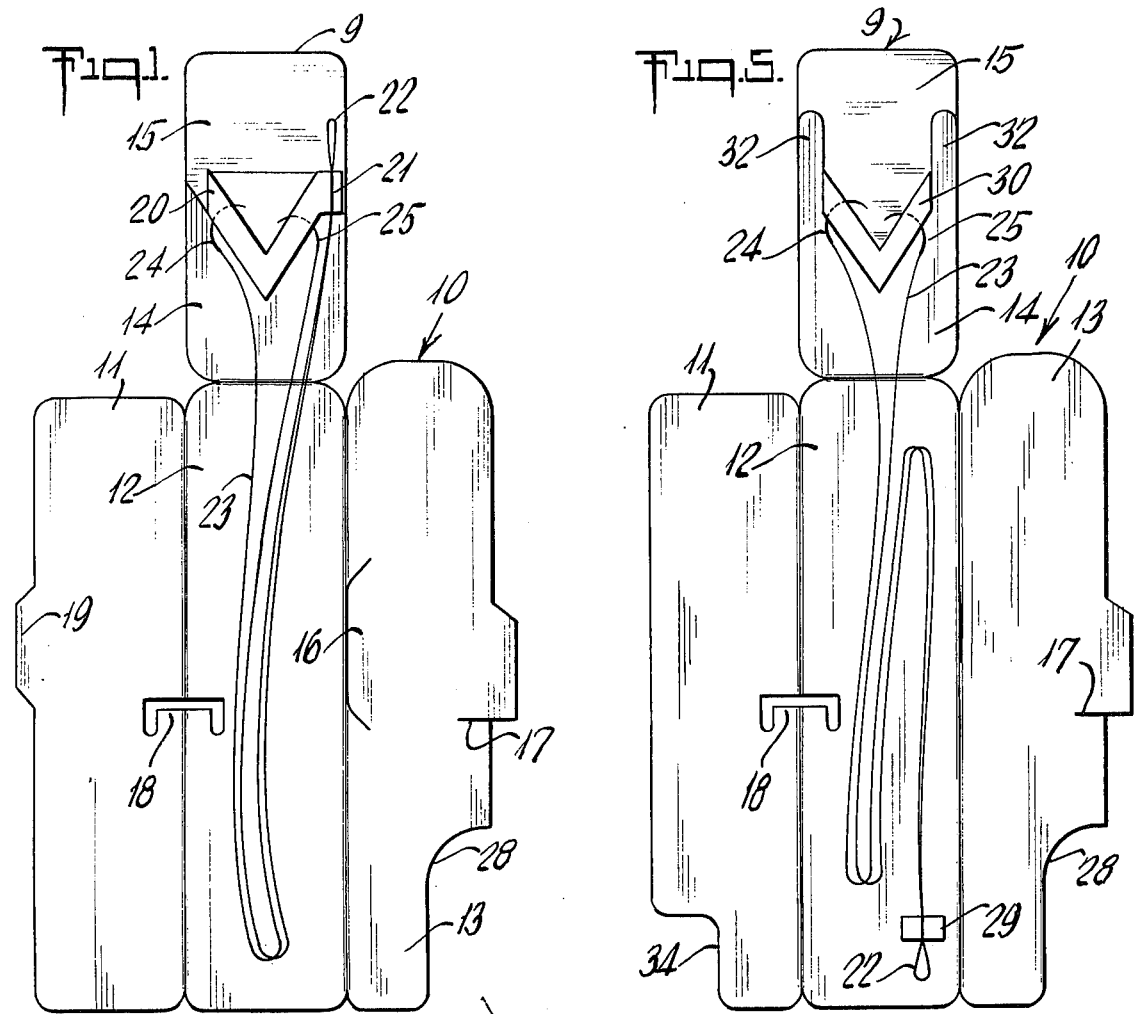
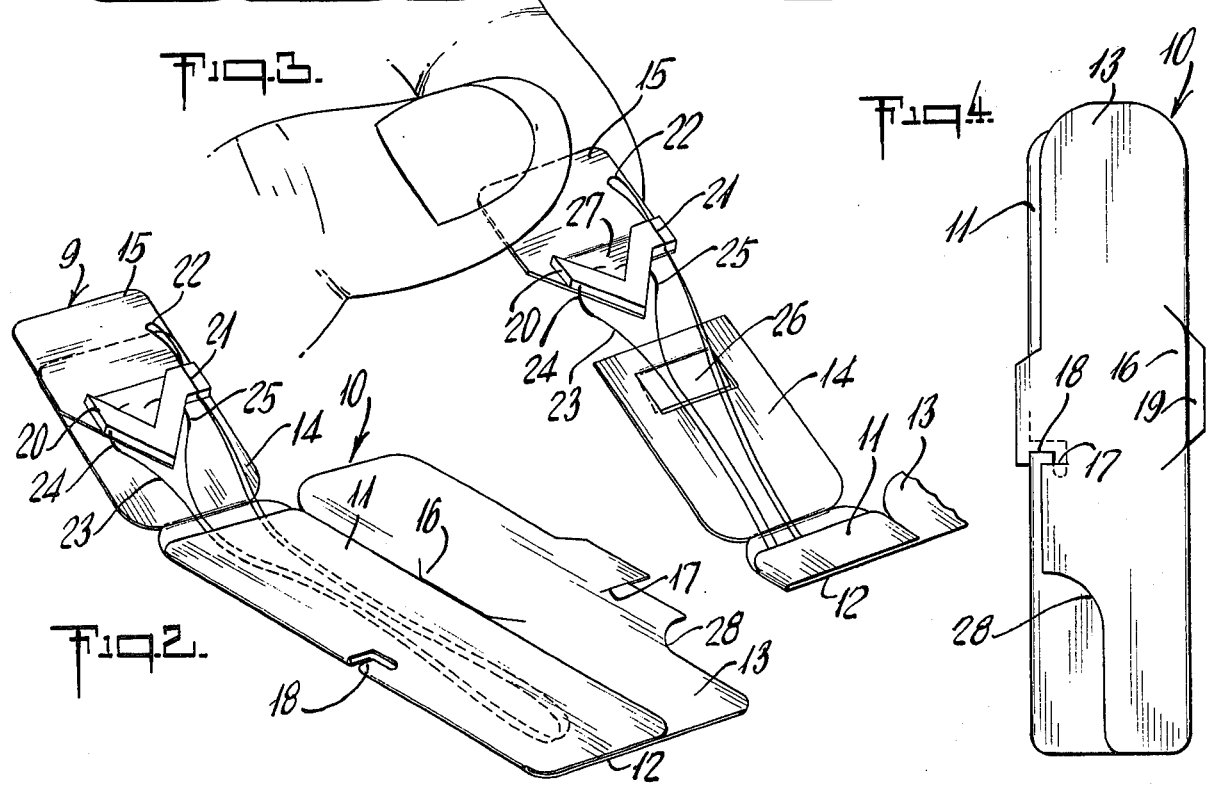

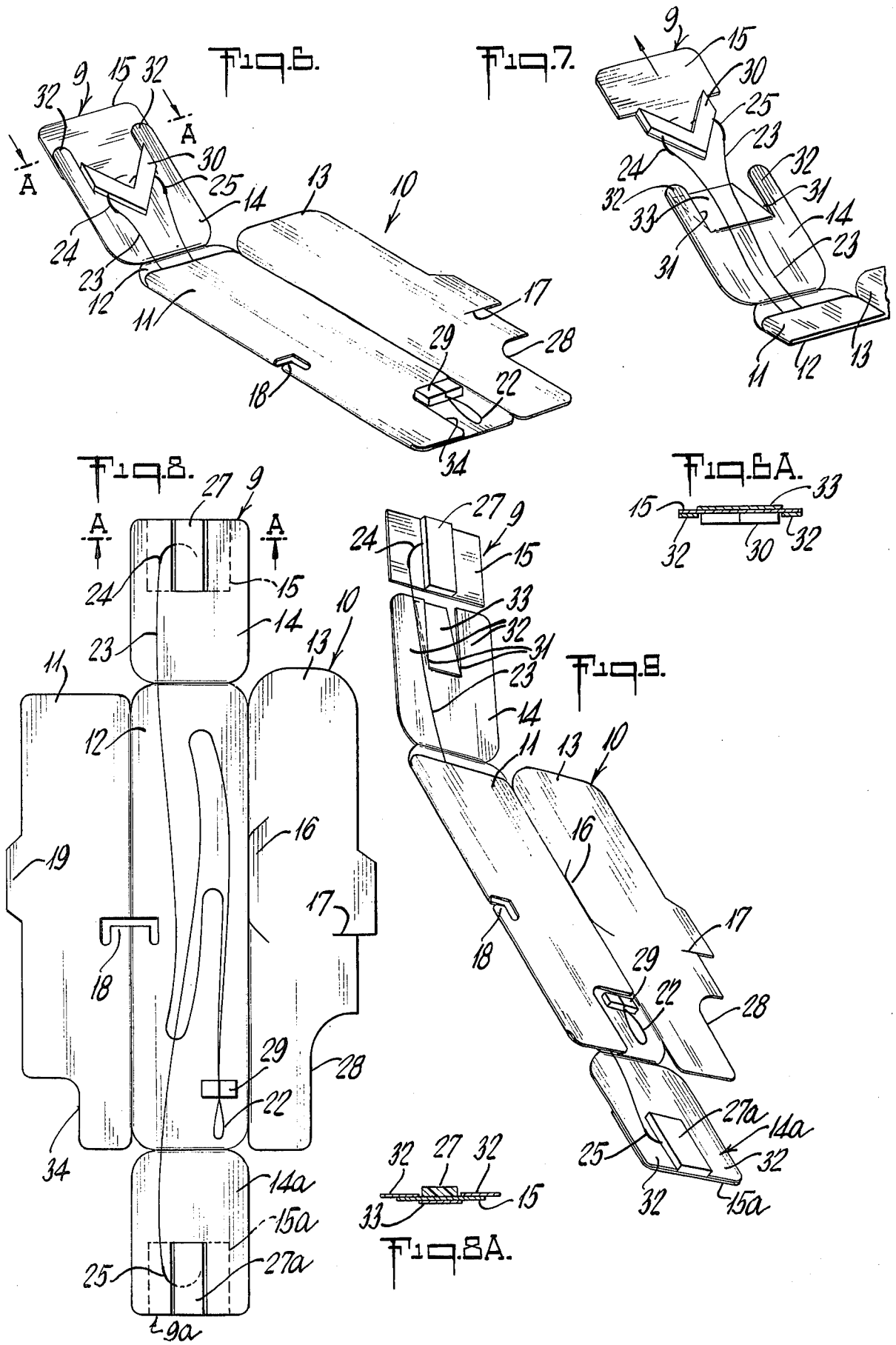

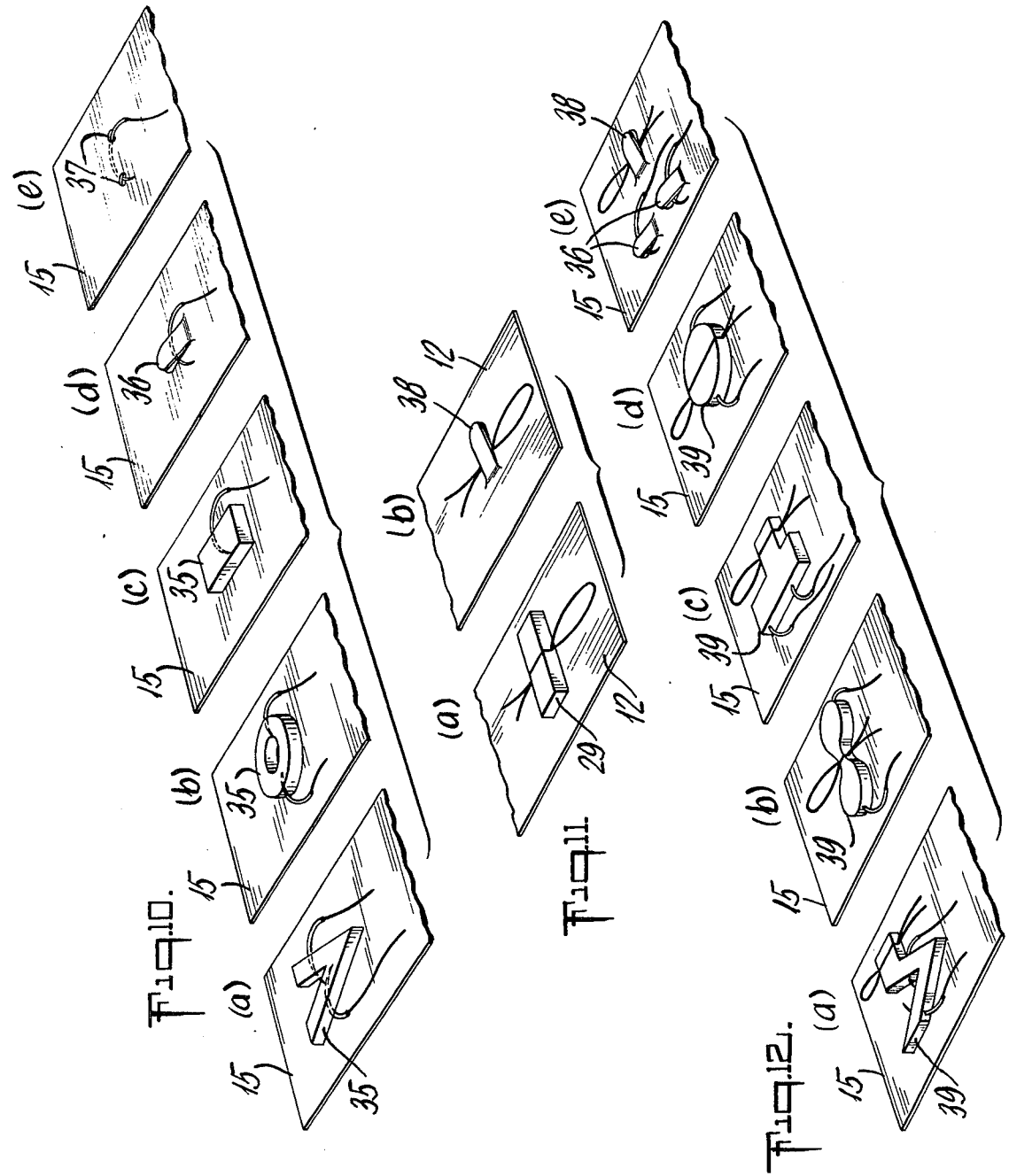

PACKAGE FOR DOUBLE-ARMED SUTURES

BACKGROUND OF THE INVENTION

1. Field of the Invention

This invention relates to surgical sutures, and more particularly to a folded paper package for double-armed ophthalmic sutures.

2. Description of Prior Art

Packages for surgical sutures are constructed according to the nature of the suture and its intended use. In general, the ideal package holds and protects the suture during handling and storage, and yet allows the suture to be readily removed with a minimum of handling.

In the case of ophthalmic sutures, the difficulty in providing a package which is convenient for the surgeon is particularly difficult due to the very fine diameter of the suture and small size of the needles. Once removed from the package, the sutures are easily lost among the towels and surgical implements in the operating field.

U.S. Pat. No. 3,951,261 describes a method of packaging ophthalmic sutures wherein the needles are held in a removable mount which aids in locating the sutures once removed from the package. The package of the present invention utilizes the concept of a needle mount as disclosed in this reference and represents an improvement over the package thereof.

Ophthalmic sutures are generally packaged as double-armed sutures in lengths of 5 to 18 inches. Although a double-armed suture is required for many ophthalmic procedures, single-armed sutures are also frequently required, and it has been the practice of ophthalmic surgeons to cut double-armed sutures in half to obtain two single-armed sutures. This is a time consuming step since the surgeon or operating room nurse must first remove the suture from the package, locate the midpoint, and then cut the suture. The problem of lost sutures is even greater in the case of single-armed sutures since the suture half not used immediately is out of the package and must be set aside without protection until needed.

It is accordingly an object of the present invention to provide a suture package for double-armed ophthalmic sutures which provides for improved storage and removal of ophthalmic sutures. It is a further object of this invention to provide a package for ophthalmic sutures in which the midpoint of the suture is identified and readily accessible for cutting before the suture is removed from the package.

It is a further object of this invention to provide a package for double-armed ophthalmic sutures which allows the suture to be cut in half either before or after removal from the package. These and other objects will be apparent from the ensuing description and claims.

SUMMARY

A folded suture package for single strand, double-armed sutures characterized in that each needle is secured in a removable needle mount, and a loop of the suture located equidistant from each needle is secured in a suture loop retainer. The needles and suture are totally contained within the confines of the folded package. When the package is opened, the needles and suture loop become readily accessible while the major portion of the suture length remains within a suture compartment between folded panels. The suture may be readily removed from the package by removing the needle mount with the needles secured therein. If desired, the suture may be cut at the suture loop to obtain two single-armed sutures of approximatley equal length before removing the suture from the package. In a preferred embodiment, the suture loop is retained by the needle mounting means so that the suture may be cut after it is removed from the package.

DESCRIPTION OF DRAWINGS

FIG. 1 is a plan view of a suture package of the present invention in a fully open position showing the individual panels of the package and the position of the suture thereon.

FIG. 2 is a view in perspective of the package of FIG. 1 in the partially open position for dispensing the suture.

FIG. 3 is a partial view of the package of FIG. 1 showing the removal of the needle mount therefrom.

FIG. 4 is a plan view of the package of FIG. 1 in a fully closed position.

FIG. 5 is a plan view of another suture package of the present invention in a fully open position.

FIG. 6 is a view in perspective of the package of FIG. 5 in the partially open position.

FIG. 6A is a sectional view of the needle mounting panel through line A—A of FIG. 6.

FIG. 7 is a partial view of the package of FIG. 5 showing the removal of the needle mount therefrom.

FIG. 8 is a plan view of a suture package of the present invention in a fully open position showing the individual panels of the package and the position of the suture thereon.

FIG. 8A is a sectional view of the needle mounting panel through line A—A of FIG. 8.

FIG. 9 is a view in perspective of the package of FIG. 8 in a partially open position for dispensing the suture.

FIG. 10 is a partial view in perspective of the package of the present invention showing five needle mounting means having different structures.

FIG. 11 is a partial view in perspective of the package of the present invention showing two suture loop retaining means having different structures.

FIG. 12 is a partial view in perspective of the package of the present invention showing five integral needle mounting and suture loop retaining means having different structures.

DESCRIPTION OF PREFERRED EMBODIMENTS

Suture packages of the present invention are characterized by a one-piece, multipanel, foldable construction which incorporates needle mounting means and suture loop retaining means within the confines of the folded package. The needle mounting means are preferably removable from the body of the package. The suture loop retaining means may be integral with the needle mounting means and removable therewith, or may be separately and permanently attached to one of the package panels.

In a preferred embodiment, the suture, needles and suture loop are all enclosed within the confines of the package when the package is in its completely folded position. When ready for use, the outer cover panels of the package are opened to expose the needles in the needle mounting means and to expose the suture loop in the suture loop retaining means while the major portion of the suture remains confined within a compartment of the package. The suture is removed from the package by removing the needle mount with the needles attached and withdrawing the length of suture from the suture compartment.

Where the surgeon requires a single-armed rather than a double-armed suture, the suture loop is cut with scissors or scalpel. Where the suture loop retaining means is integral with the needle mounting means, the suture loop may be cut either before or after removing the suture from the package so long as the needles and suture loop remain secure in the mounting means. Where the suture loop retaining means is mounted in the package and separate from the needle mounting means, it will be appreciated that it is necessary to cut the suture loop before removing the suture from the package.

Referring now to FIGS. 1-4, there is shown one preferred package of the present invention having integral and removable needle mounting and suture loop retaining means. FIG. 1 illustrates the package in a fully open position. Package 10 is comprised of center panel 12, first cover panel 11, second cover panel 13, needle mounting panel 14, and needle mounting means 9 removably attached to panel 14. Needle mounting means 9 comprises a flat paperboard base 15 having a three-dimensional, pierceable body 20 secured thereon. Suture 23 having needles 24 and 25 inserted into body 20 is looped or coiled on center panel 12 with suture loop 22 retained in slit 21 of body 20.

Referring now to FIG. 2, there is illustrated the package of FIG. 1 with cover panel 11 folded over center panel 12 enclosing suture 23 therebetween. Tab 19 and panel 11 interlocks with slot 16 of panel 13 to maintain the panel in the folded position. Panel 14 is subsequently folded forward over panel 11 and cover panel 13 is folded over panels 14 and 11 to form the completely folded package illustrated in FIG. 4. Slit 17 in panel 13 interlocks with tab 18 in panels 11 and 12 as illustrated in FIG. 4 to maintain panel 13 in its folded position.

To remove the suture from the package, the completely folded package of FIG. 4 is partially opened to the position of FIG. 2 and needle mounting means 9 is grasped by base 15 and removed from panel 14 as illustrated in FIG. 3. As shown in FIG. 3, base 15 contains Vee-tab 27 which is inserted in slot 26 of panel 14 when base 15 is in position on panel 14. Once removed from the package, the suture is readily located by virtue of the easily recognized needle mount, and the needles may be grasped with a needle holder and removed from the needle mount.

As further illustrated in FIG. 3, the suture loop remains secured in slit 21 of body 20 as base 15 is removed from panel 14. If single-armed sutures are desired, suture loop 22 may be cut any time before needle 24 and 25 is removed from body 20. One suture may then be removed from body 20 while the other remains secured thereon for later use.

Referring now to FIG. 5, there is illustrated a suture package wherein the suture loop retaining means is separate from the needle mounting means and is permanently attached to center panel 12. The suture loop retaining means comprises a three-dimensional, resilient body 29 having a suture receiving slit 29 therein with suture loop 22 extending therefrom. Needle mounting means 9 comprises a flat base element 15 having a three-dimensional, resilient pierceable body 30 mounted thereon.

Panel 11 of package 10 in FIG. 5 has cutout 34 extending over the area of suture loop 22 and suture loop retaining means 29 when panel 11 is folded over panel 12 as illustrated in FIG. 6. In this particular embodiment of the package, the interlocking tab and slot of panels 11 and 13, respectively, which are evident in the package of FIG. 1 have been omitted since they are not essential to the packages of the present invention. The package is completely folded and locked in position by folding panel 13 over panel 11 and interlocking tab 18 with slit 17 as aforedescribed with reference to the package of FIG. 1.

Referring now to FIG. 7, panel 14 has two slits 31 extending from the top thereof to form tongue 33 and side tabs 32. Suture mounting means 9 is removably secured to panel 14 by slipping base 15 over tongue 33 and under tabs 32 as illustrated in FIG. 6 and in the sectional view in FIG. 6A.

Since the suture loop retaining means of the package of FIG. 6 is permanently attached to the body of the package, it will be appreciated that the suture loop 22 must be cut before removing needle mount 9 from panel 14 if single-armed sutures are desired. When needle mount 9 is removed and suture 23 is withdrawn from between panels 11 and 12, suture loop 22 is pulled free of body 29 and a double-armed suture will result unless the suture loop has been previously severed.

Turning now to FIG. 8, there is illustrated a modified package wherein package 10 is provided with dual needle mounting panels 14 and 14a at either end of panel 12, and individual needle mounting means 9 and 9a are provided for each needle of the double-armed suture. As illustrated in FIG. 9, panel 14 contains end slots 31 forming tonque 33 and side tabs 32. Needle mounting means 9 comprises a three-dimensional, resilient, pierceable rectangular body 27 mounted on flat, rectangular base 15. The width of body 27 is slightly smaller than the width of tongue 33 to allow means 9 to be mounted on panel 14 by inserting base 15 over tongue 33 and under side tabs 32 as illustrated in FIG. 8 and the sectional view of FIG. 8A. Needle mount 9a and panel 14a are substantial duplicates of needle mount 9 and panel 14.

The package of FIG. 8 is closed and locked by folding panel 11 over panel 12 as shown in FIG. 9, and thereafter folding panels 14 and 14a inward over panel 11 and folding cover panel 13 over panels 14, 14a and 11 with tab 18 interlocking with slit 17 as herebefore described with reference to FIG. 1.

FIG. 10 illustrates various needle mounting means which may be utilized in the packages of the present invention. FIGS. 10 (a), (b), and (c) illustrate various configurations of three-dimensional, resilient, pierceable bodies 35, while FIG. 10 (d) illustrates a tab 36 cut in base 15 with the needle inserted thereunder. FIG. 10 (e) illustrates a double aperture 37 in base 15 with the needle inserted therethrough.

FIG. 11 illustrates various suture loop retaining means which may be utilized in the packages of the present invention. FIG. 11 (a) illustrates a three-dimensional resilient body 29 having a suture receiving slit therein, while FIG. 11 (b) illustrates a tab 38 cut in a panel of the package with the suture loop inserted thereunder.

FIG. 12 illustrates various configurations of integral needle mounting and suture loop retaining means which may be utilized in the present invention. FIGS. 12 (a)-(d) illustrate three-dimensional, resilient, pierceable bodies 39 having a suture receiving slit therein. FIG. 12 (e) illustrates three tabs cut into base 15 with the suture needles mounted under tabs 36 and the suture loop retained under tab 38.

Preferred needle mounting and suture loop retaining means comprise three-dimensional, resilient, pierceable bodies as described above. Such bodies may be formed of silicone rubber, silicone foam, polyurethane, polystyrene, collagen sponge, polyethylene foam, and the like. The basic requirements of such materials are that they be sufficiently soft to permit penetration by delicate ophthalmic needles, and sufficiently resilient to secure the needle once inserted. Bodies having a thickness of about 0.15 to 0.20 cm allow convenient insertion of the needle and, when slit one-half to two-thirds of the thickness, are effective to retain a suture loop inserted in the slit.

Many needle mounting and suture loop retaining means other than those illustrated herein will be apparent to those skilled in the art, and the present invention is accordingly not limited to any particular illustrated configuration. It is also apparent that the configuration of the panels of package 10 may be modified without departing from the scope of the present invention, the essential element of which is to provide in combination needle mounting means and suture loop retaining means whereby the midpoint of the suture is identified and accessible for cutting when the package is opened.

The packages of the present invention are preferably enclosed in an outer envelope and sterilized prior to use in accordance with conventional suture packaging and sterilization procedures. The packages of the present invention are useful with all suture materials, absorbable and nonabsorbable, natural or man-made. The foregoing specification is accordingly by way of description and illustration, and the present invention is not to be limited to the specific form or arrangement of parts as described or shown herein.

What is claimed is:

1. A folded package for a double-armed suture comprising
   (a) a center panel, a first and second cover panel foldably attached to said center panel along two sides thereof, and a needle mounting panel foldably attached to said center panel along a third side thereof,
   (b) needle mounting means on said needle mounting panel,
   (c) suture loop retaining means on one of said panels, and
   (d) a double-armed suture contained in said package having both needles secured in said needle mounting means and a suture loop substantially equidistant from each needle secured in said suture loop retaining means,
      said first cover panel of said package being folded over said center panel with a major portion of said suture enclosed therebetween,
      said needle mounting panel being folded over said first cover panel with said needles and needle mounting means enclosed therebetween, and
      said second cover panel being folded over said needle mounting panel and first cover panel with said suture loop retaining means enclosed therebetween,
      whereby when the second cover panel and needle mounting panel are unfolded from said center panel, said needles and said suture loop are readily accessible and said suture may be cut at said loop to obtain two single-armed sutures of substantially equal length before removing said suture from between said folded panels.

2. Package of claim 1 wherein said suture loop retaining means is attached to said center panel and said first cover panel has a cutout over the position of said suture loop retaining means and the suture loop therein.

3. Package of claim 1 having a second needle mounting panel foldably attached to said center panel along a fourth side thereof with a second needle mounting means on said second needle mounting panel.

4. A package of claim 3 wherein one needle of said double-armed suture is secured in each of said needle mounting means.

5. Package of claim 1 wherein said needle mounting means comprises a three-dimensional, self-sustaining, resilient, pierceable body.

6. Package of claim 5 wherein said suture loop retaining means comprises a three-dimensional, self-sustaining, resilient body having a suture loop accepting slit therein.

7. Package of claim 6 wherein said suture loop retaining means is integral with said needle mounting means.

8. Package of claim 5 wherein said needle mounting means is attached to a base comprising a flat card member having flat surface dimensions larger than those of the three-dimensional body.

9. Package of claim 8 wherein said needle mounting panel contains slot means cooperating with said base of said needle mounting means for removably securing said needle mounting means to said needle mounting panel.

10. Package of claim 1 wherein said suture loop retaining means comprises a suture receiving tab in said center panel.

11. Package of claim 1 wherein said needle mounting means comprises a needle receiving tab in said needle mounting panel.

12. A folded package for a double-armed suture comprising
   (a) an elongated center panel having a major and minor axis, a first and a second cover panel foldably attached to said center panel along the major sides thereof, an a needle mounting panel foldably attached to said center panel along one minor side thereof,
   (b) needle mounting means comprising a three-dimensional, self-sustaining, resilient, pierceable body mounted on said needle mounting panel,
   (c) suture loop retaining means comprising a three-dimensional, self-sustaining, resilient body having a suture loop accepting slit therein mounted on one of said panels, and
   (d) a double-armed suture contained in said package having both needles secured in said needle mounting means and a suture loop substantially equidistant from each needle secured in said suture loop retaining means,
      said first cover panel of said package being folded over said center panel with a major portion of said suture enclosed therebetween,
      said needle mounting panel being folded over said first cover panel with said needles and needle mounting means enclosed therebetween, and
      said second cover panel being folded over said needle mounting panel and first cover panel with said suture loop retaining means enclosed therebetween, whereby when the second cover panel and needle mounting panel are unfolded from said center panel, said needles and said suture loop are readily accessible and said suture may be cut at said loop to obtain two single-armed sutures of substantially equal length before removing said needles from said needle mount.

13. Package of claim 12 wherein said needle mounting means is attached to a base comprising a flat card member having flat surface dimensions larger than those of the three-dimensional body.

14. Package of claim 13 wherein said needle mounting panel contains slot means cooperating with said base of said needle mounting means for removably securing said needle mounting means to said needle mounting panel.

15. Package of claim 12 wherein said suture loop retaining means is integral with said needle mounting means.

16. Package of claim 12 wherein said sutur loop retaining means is attached to said center panel and said first cover panel has a cutout over the position of said suture loop retaining means and the suture loop therein.

17. Package of claim 12 having a second needle mounting panel foldably attached to said center panel along the other minor side thereof with a second needle mounting means comprising a three-dimensional, self-sustaining, resilient, pierceable body mounted on said second needle mounting panel.

18. Package of claim 12 wherein said first and second cover panels have integral locking means to maintain said first panel in its folded position over said center panel.

19. Package of claim 18 wherein said integral locking means comprises a tab on the unattached major side of said first cover panel, and a corresponding tab receiving slit in the second cover panel along the line of attachment of said second cover panel to said center panel.

20. Package of claim 12 wherein said first cover and center panels have integral locking means to maintain said second cover panel in its folded position over said needle mounting panel and first cover panel.

21. Package of claim 20 wherein said integral locking means comprising a tab along the folded edge of said first cover panel and said center panel and a corresponding tab receiving slit in the unattached major edge of said second cover panel.

* * * * *

UNITED STATES PATENT AND TRADEMARK OFFICE
CERTIFICATE OF CORRECTION

PATENT NO. : 4,120,395
DATED : October 17, 1978
INVENTOR(S) : Harvey B. Mandel et al.

It is certified that error appears in the above—identified patent and that said Letters Patent is hereby corrected as shown below:

Column 3, line 52, "needle 24 and 25" should read

-- needle 24 or 25 --.

Claim 16, line 22, "said sutur" should read

-- said suture --.

Claim 21, line 21, "comprising" should read

-- comprises --.

*Signed and Sealed this*

*Twenty-seventh* Day of *November 1979*

[SEAL]

Attest:

RUTH C. MASON
*Attesting Officer*

LUTRELLE F. PARKER
*Acting Commissioner of Patents and Trademarks*